United States Patent
Lin et al.

(10) Patent No.: US 9,370,540 B2
(45) Date of Patent: Jun. 21, 2016

(54) K2 COMPOSITION AND THE PREPARATION METHOD AND USE OF THE SAME

(71) Applicant: SINPHAR PHARMACEUTICAL CO., LTD., Dongshan Township, Yilan County (TW)

(72) Inventors: Hang-Ching Lin, Dongshan Township, Yilan County (TW); Hsin-Wen Huang, Dongshan Township, Yilan County (TW); Shih-Min Lu, Dongshan Township, Yilan County (TW)

(73) Assignee: SINPHAR PAHRMACEUTICAL CO., LTD., Dongshan Township, Yilan County (TW)

( * ) Notice: Subject to any disclaimer, the term of this patent is extended or adjusted under 35 U.S.C. 154(b) by 0 days.

(21) Appl. No.: 14/717,440

(22) Filed: May 20, 2015

(65) Prior Publication Data

US 2015/0335690 A1    Nov. 26, 2015

Related U.S. Application Data

(60) Provisional application No. 62/001,328, filed on May 21, 2014, provisional application No. 62/001,737, filed on May 22, 2014.

(51) Int. Cl.
*A61K 36/00* (2006.01)
*A61K 36/076* (2006.01)
*A61K 31/575* (2006.01)
*C07J 9/00* (2006.01)

(52) U.S. Cl.
CPC ............. *A61K 36/076* (2013.01); *A61K 31/575* (2013.01); *C07J 9/005* (2013.01); *A61K 2236/00* (2013.01)

(58) Field of Classification Search
None
See application file for complete search history.

(56) References Cited

U.S. PATENT DOCUMENTS

2009/0247496 A1 * 10/2009 Lin ..................... A61K 9/485
                                                      514/181
2010/0279992 A1    11/2010 Lin

FOREIGN PATENT DOCUMENTS

| CN | 1035051 | 8/1989 |
|---|---|---|
| EP | 2 305 268 | 4/2011 |
| JP | 09040552 A * | 2/1997 |
| WO | 2009155730 | 12/2009 |
| WO | 2010127557 | 11/2010 |

OTHER PUBLICATIONS

Keller, Antimicrobial steroids from the fungus Fomitopsis pinicola. Phytochemistry, (Mar. 1996) vol. 41, No. 4, pp. 1041-1046.*
International Search Report and Written Opinion of International Application No. PCT/CN2015/079439 mailed Aug. 18, 2015/.
Ke, Li, M.S. thesis, "Isolation, Purification, Structure Elucidation of Triterpenoids from Surface Layer of Poria cocos and Study on Fingerprints of Traditional Chinese Medicine Poria Cocos (Schw.) Wolf", Hubei University of Chinese Medicine, 2013.
Hui, Ling, Ph.D. dissertation, "Evaluation of the chemotherapeutic and chemopreventive potential of triterpenoids from Poria cocos", National University of Singapore, 2010.
Si-Fang, Zhang et. al, "A review of chemical constituents, medicinal function, development and utilization of Poria cocos", Chinese Journal of Integrated Traditional and Western Medicine, 2005, vol. (18) No. 2, pp. 227-230.
Zong-Hua, Song et. al, "Pharmacokinetic Study of Dehydrotumulosic Acid in Rat Plasma after Oral Administration of Poriatin", Chinese Journal of Pharmaceutical Analysis, 2002, No. 3, pp. 228-231.
Zheng, Y., and Yang X.W. (2008). Absorption and transport of pachymic acid in the human intestinal cell line Caco-2 monolayers. Zhong xi yi jie he xue bao = Journal of Chinese integrative medicine 6, 704-710.
Ling, H., Jia, X., Zhang, Y., Gapter, L.A., Lim, Y.S., Agarwal, R., and Ng, K.Y. (2010). Pachymic acid inhibits growth and modulates arachidonic acid metabolism in nonsmall cell lung cancer A549 cells. Molecular carcinogenesis 49, 271-282.
Ling, H., Zhou, L., Jia, X., Gapter, L.A., Agarwal, R., and Ng, K.Y. (2009). Polyporenic acid C induces caspase-8-mediated apoptosis in human lung cancer A549 cells. Molecular carcinogenesis 48, 498-507.

* cited by examiner

*Primary Examiner* — Qiuwen Mi
(74) *Attorney, Agent, or Firm* — Ping Wang; Andrews Kurth LLP

(57) ABSTRACT

A method for providing a K2-enriched FU-LING extract is provided. The method comprises the following steps:
(a) mixing a FU-LING with a solvent to provide a first mixture;
(b) alkalizing the first mixture to provide a second mixture;
(c) acidifying the second mixture to provide a third mixture,
(d) alkalizing the third mixture to provide a fourth mixture, wherein the fourth mixture has a pH value of more than 7; and
(e) neutralizing the forth mixture,
wherein the K2 is at least one of tumulosic acid, dehydrotumulosic acid, polyporenic acid C and 3-epi-dehydrotumulosic acid.

20 Claims, 3 Drawing Sheets

K2 COMPOSITION AND THE PREPARATION METHOD AND USE OF THE SAME

This application claims priority to U.S. Provisional Application No. 62/001,328 filed on May 21, 2014 and U.S. Provisional Application No. 62/001,737 filed on May 22, 2014, in the United State Patent and Trademark Office, and to Taiwan Patent Applicant No. 104116013 filed on Apr. 20, 2015, in the Taiwan Intellectual Property Office, the disclosures of which are incorporated herein in their entirety by reference.

BACKGROUND OF THE INVENTION

1. Field of the Invention

The present invention relates to a method for converting pachymic acid and/or dehydropachymic acid in a material into tumulosic acid, dehydrotumulosic acid, polyporenic acid C and/or 3-epi-dehydrotumulosic acid effectively, so as to provide a product which is substantially free of pachymic acid and dehydropachymic acid. The product thus obtained can be further processed to provide a K2 composition that is enriched with tumulosic acid, dehydrotumulosic acid, polyporenic acid C and/or 3-epi-dehydrotumulosic acid. The aforementioned product and K2 composition can be used for treating cancers, in particular, for treating lung cancer.

2. Description of the Related Art

Researches have proven that triterpenoids such as pachymic acid, dehydropachymic acid, tumulosic acid, dehydrotumulosic acid, polyporenic acid C, and 3-epi-dehydrotumulosic acid are effective in such as diuresis, anti-oxidation, anti-cancer, anti-inflammation, anti-hyperglycemia, and immunoregulation. Although the triterpenoids have great efficacy and are potential in disease treatments, so far it is hard to synthesize the triterpenoids and their preparation methods are still unavailable. The triterpenoids currently used in industry are primarily obtained from the extract of FU-LING (*Poria cocos*) and/or the metabolic products of FU-LING, and it is hard to obtain the triterpenoids from other plants or fungi and the fermentation products thereof.

The research results have proven that, as compared to other triterpenoids of FU-LING, pachymic acid and dehydropachymic acid in the extract of FU-LING are less soluble in water, and this characteristic causes a great inconvenience to their application on disease treatments. For example, after administering a drug or a FU-LING extract that contains pachymic acid and/or dehydropachymic acid to a subject, the poor solubility of pachymic acid and dehydropachymic acid may adversely affect the treatment and control of diseases, and this is a task in this field extremely desired to be solved. Relevant description can be seen in such as "Absorption and transport of pachymic acid in the human intestinal cell line Caco-2 monolayers. *Journal of Chinese integrative medicine*. 6:704-710 (2008)", which is entirely incorporated hereinto by reference.

In addition, the amounts of and proportion among pachymic acid, dehydropachymic acid, tumulosic acid, dehydrotumulosic acid, polyporenic acid C and 3-epi-dehydrotumulosic acid in a FU-LING medicinal material depend on the conditions such as growth environment, weather, and soil for planting the FU-LING, and this causes the combination of triterpenoids in FU-LING medicinal materials from different habitats/batches unstable and renders FU-LING medicinal materials not suitable for therapeutic purposes. Accordingly, for the application of the aforementioned triterpenoids in disease treatments, how to lead a subject after being administered with triterpenoids to acquire a stable amount of active ingredient is another task in this field extremely desired to be solved.

Furthermore, the manufacture of a triterpenoid medicament that contains tumulosic acid, dehydrotumulosic acid, polyporenic acid C and 3-epi-dehydrotumulosic acid only may meet the requirements of manufacturing a medicament with consistent components, reproducibility, consistent quantity, and quality control, and the inventors have found that this could be achieved by converting pachymic acid and dehydropachymic acid into tumulosic acid, dehydrotumulosic acid, polyporenic acid C and 3-epi-dehydrotumulosic acid to provide consistent components (various pre-experiments have proven that the proportion of components is approximately consistent). The present invention is directed to the discovery and also directed to the therapeutic effects of the converted products.

China Patent Application No. 00119304.X (Inventors: Dr. Xu Jin, etc.) alleges that an extract with triterpenoids at a content more than 70 wt % can be provided by organic extracting and alkalizing FU-LING However, the inventors of the present invention repeated the experiments of the said Chinese patent application and the results revealed that the real content of triterpenes is merely about 40%. It is believed that the inaccurate analysis results of China Patent Application No. 00119304.X (Inventors: Dr. Xu Jin, etc.) are resulted from the use of oleanolic acid color reaction analysis as the examination method. On the other hand, the inventors of the present invention adopted a FU-LING triterpene standards examination method to examine the content of triterpenoids. Furthermore, the inventors of the present invention found that the extraction and alkalization process of China Patent Application No. 00119304.X could not provide a FU-LING extract with a content of triterpenes over 50% because of the presence of phospholipids in FU-LING. On the other hand, the present invention comprises conducting a saponification process after the organic extraction process, this operation removes phospholipids and leads the content of triterpenoids to be more than 50% and to suitable for therapeutic purposes.

The present invention is directed to the results of the research for the above requirements. The inventors of the present invention found a method for providing a product that is substantially free of K1, and the product can be further processed to provide a K2-enriched composition to achieve the purposes of enriching K2 and meet the requirements of manufacturing a medicament with consistent components, reproducibility, consistent quantity, and quality control, thereby solving the aforementioned tasks effectively, wherein the K1 is at least one of pachymic acid and dehydropachymic acid, and the K2 is at least one of tumulosic acid, dehydrotumulosic acid, polyporenic acid C and 3-epi-dehydrotumulosic acid.

SUMMARY OF THE INVENTION

Therefore, an objective of the present invention is to provide a method for providing a product which is substantially free of K1, comprising:
(a) mixing a K1-containing material with a solvent to provide a first mixture;
(b) alkalizing the first mixture to provide a second mixture; and
(c) acidifying the second mixture to provide a third mixture, wherein the K1 is at least one of pachymic acid and dehydropachymic acid, and the K2 is at least one of tumulosic acid, dehydrotumulosic acid, polyporenic acid C and 3-epi-dehydrotumulosic acid. Optionally, after the step (c), the method may further comprise performing a solid-liquid separation (e.g. centrifuge, decantation) on the third mixture to remove the liquid and retain the insoluble.

Another objective of the present invention is to provide a method for providing a K2-enriched FU-LING extract, comprising:
(a) mixing a FU-LING with a solvent to provide a first mixture;
(b) alkalizing the first mixture to provide a second mixture;
(c) acidifying the second mixture to provide a third mixture;
(d) alkalizing the third mixture to provide a fourth mixture, wherein the fourth mixture has a pH value of more than 7; and
(e) neutralizing the fourth mixture,
wherein the K2 is at least one of tumulosic acid, dehydrotumulosic acid, polyporenic acid C and 3-epi-dehydrotumulosic acid. Optionally, after the step (c), the method may further comprise performing a solid-liquid separation (e.g. centrifuge, decantation) on the third mixture to remove the liquid and retain the insoluble, and the retained insoluble is alkalized in the step (d).

Yet another objective of the present invention is to provide a product obtained from either of the above methods. Preferably, the product is substantially free of pachymic acid and dehydropachymic acid.

Yet another objective of the present invention is to provide a FU-LING extract, which is substantially free of pachymic acid and dehydropachymic acid.

Yet another objective of the present invention is to provide a use of the above product or FU-LING extract in the manufacture of a medicament for the treatment of cancers. Preferably, the medicament is for treating lung cancer.

Yet another objective of the present invention is to provide a method for treating cancers, comprising administering to a subject in need of a therapeutically effective amount of the above medicament. Particularly, the method is for treating lung cancer.

DETAILED DESCRIPTION OF THE INVENTION

Figure 1A:
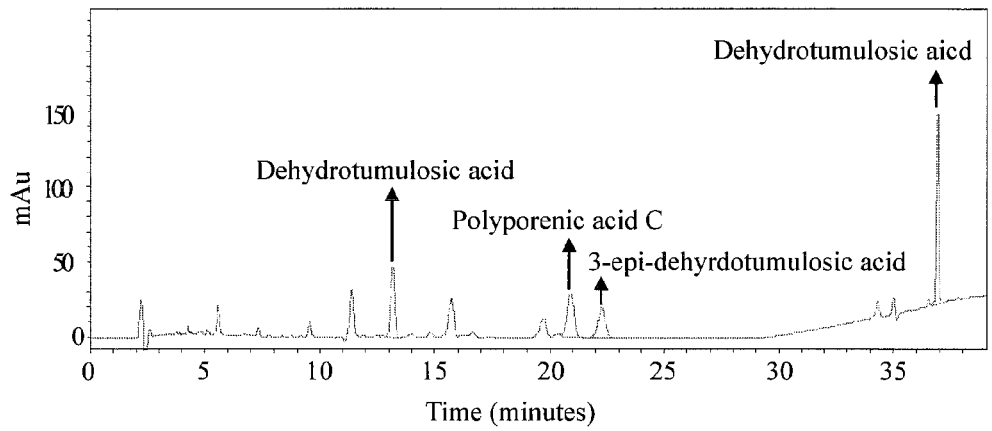
FIG. 1A is an LC/UV/MS spectrum of the raw material used in one embodiment of the conversion method of the present invention at 243 nm, showing the ingredients contained in the raw material.

The following will describe some embodiments of the present invention in detail. However, without departing from the spirit of the present invention, the present invention may be embodied in various embodiments and should not be limited to the embodiments described in the specification. In addition, unless otherwise stated herein, the expressions "a," "the," and the like recited in this specification (especially in the claims) are intended to include the singular and plural forms. In addition, the term "about", "approximately" or "almost" used in this specification substantially represents within ±20% of the stated value, preferably within ±10% and more preferably within ±5%. The term "effective amount" of "therapeutically effective amount" used in this specification refers to the amount of the medicament that can at least partially alleviate the condition that is being treated in a suspected subject when administered to the subject in need. The term "subject" used in this specification refers to a mammalian, including human and non-human animals.

As described above, the present invention provides a method for providing a product which is substantially free of K1, comprising:
(a) mixing a K1-containing material with a solvent to provide a first mixture;
(b) alkalizing the first mixture to provide a second mixture; and
(c) acidifying the second mixture to provide a third mixture, wherein the K1 is at least one of pachymic acid and dehydropachymic acid, and the K2 is at least one of tumulosic acid, dehydrotumulosic acid, polyporenic acid C and 3-epi-dehydrotumulosic acid.

Optionally, after the acidification step (c), the method of the present invention may further comprise performing a solid-liquid separation (e.g., centrifuge, decantation) on the third mixture to remove the liquid and retain the insoluble.

The method of the present invention can be used in any suitable materials containing pachymic acid and/or dehydropachymic acid. In general, the materials can be pachymic acid and/or dehydropachymic acid themselves or be other matters containing pachymic acid and/or dehydropachymic acid. In one embodiment of the present invention, the K1-containing material in step (a) is a FU-LING (*Poria cocos*) extract, wherein the extract contains pachymic acid, dehydropachymic acid, tumulosic acid, dehydrotumulosic acid, polyporenic acid C and 3-epi-dehydrotumulosic acid.

Step (a) could be performed by directly adding the K1-containing material into a container with the solvent, or by adding the solvent into a container with the K1-containing material, and then agitating the mixture to provide the first mixture. The solvent can be water, C1-C4 alcohol, or a mixture of water and C1-C4 alcohol. In general, there is no particular limitation to the amount of the solvent used, as long as the material can be dispersed evenly. In one embodiment of the present invention, in the step (a), water was used as the solvent, and the K1-containing material was dispersed in water at a volume ratio of material:water=1:10.

In the present invention, the term "alkalizing" refers to the increment in the pH value of the matter. In step (b) of the conversion method of the present invention, any suitable alkaline substance can be used to increase the pH value of the first mixture, and to perform the desired alkalizing reaction to provide the second mixture. Examples of the alkaline substance include, but are not limited to, alkaline metal hydrides (e.g., sodium hydride, potassium hydride), alkaline metal hydroxides (e.g., sodium hydroxide, potassium hydroxide), alkaline metal alkoxides (e.g., sodium methoxide, potassium methoxide, sodium ethoxide, potassium ethoxide, lithium tert-butoxide, sodium tert-butoxide, potassium tert-butoxide), alkyl lithiums (e.g., n-butyllithium, sec-butyllithium, tert-butyllithium, n-hexyllithium), hydroxides of alkaline earth metals (e.g., magnesium hydroxide, calcium hydroxide), carbonates (e.g., sodium carbonate, potassium carbonate, cesium carbonate), and bicarbonates (e.g., sodium bicarbonate, potassium bicarbonate, ammonium bicarbonate). Preferably, in step (b), one or more of alkaline metal hydroxides, carbonates and bicarbonates, such as sodium hydroxide, potassium hydroxide, potassium bicarbonate, sodium bicarbonate, potassium carbonate, and/or sodium carbonate are used. In one embodiment of the present invention, sodium hydroxide was used to perform the alkalizing step (b).

Generally, in step (b), the pH value of the first mixture is increased to be no less than about 10, preferably no less than about 11, and more preferably no less than about 12. In one embodiment of the present invention, in the step (b), sodium hydroxide was added into the first mixture at an amount of about 1N sodium hydroxide in the first mixture, to increase the pH value of the first mixture to about 12.

After the pH value of the first mixture has been increased, the alkalizing reaction is performed at an elevated temperature. For example, the alkalizing reaction is performed at temperature of at least 50° C., preferably at least 60° C. As shown in the examples provided hereinafter, the alkalizing reaction of the step (b) was performed at temperature of about 60° C., about 65° C., or about 70° C., to provide a second mixture.

Then, the acidification reaction of step (c) is performed, wherein an acid is added into the second mixture to decrease its pH value, and thus a third mixture is provided.

Any suitable acidic substance can be added into the second mixture to decrease its pH value, to perform a desired acidification reaction. Examples of suitable acidic substances include, but are not limited to, inorganic acids (e.g., hydrochloric acid, hydrobromic acid, sulfuric acid, sulfamic acid, nitric acid, phosphoric acid) and organic acids (e.g., acetic acid, trifluoroacetic acid, formic acid). Preferably, an inorganic acid is used in step (c) to decrease the pH value of the second mixture. In one embodiment of the present invention, hydrochloric acid was used in step (c) to decrease the pH value of the second mixture.

There is no particular limitation to the level of decrease of the pH value of the second mixture, as long as the pH value is decreased. Generally, the pH value of the second mixture is decreased for at least about 3.0 (such as being decreased from 10.0 to 7.0), preferably for at least about 4.0. In one embodiment of the present invention, in the acidifying step (c), the pH value of the second mixture was decreased to about 7 to provide the third mixture.

As showed in the examples provided hereinafter, the third mixture provided in the step (c) of the present invention is substantially free of pachymic acid and dehydropachymic acid, and the total content of pachymic acid, dehydropachymic acid, tumulosic acid, dehydrotumulosic acid, polyporenic acid C and 3-epi-dehydrotumulosic acid contained in the third mixture is higher than that contained in the K1-containing material used in step (a).

The term "substantially free of pachymic acid and dehydropachymic acid" herein refers to that, in a product, the total content of pachymic acid and dehydropachymic acid is no more than about 20 wt %, preferably no more than 10 wt %, more preferably no more than 5 wt %, and especially preferably no more than 0.5 wt %, based on the total weight of pachymic acid, dehydropachymic acid, tumulosic acid, dehydrotumulosic acid, polyporenic acid C and 3-epi-dehydrotumulosic acid contained in the product. In one embodiment of the present invention, the total content of pachymic acid and dehydropachymic acid in the product obtained from the conversion method of the present invention is about 0 wt %, i.e., less than 0.5 wt %, based on the total weight of pachymic acid, dehydropachymic acid, tumulosic acid, dehydrotumulosic acid, polyporenic acid C and 3-epi-dehydrotumulosic acid contained in the product.

The present inventors found that, when FU-LING extract is used as the K1-containing material, the following steps can be performed to further increase the content of K2 after step (c):
(d) alkalizing the third mixture to provide a fourth mixture, wherein the fourth mixture has a pH value of more than 7; and
(e) neutralizing the fourth mixture, In step (d), any suitable alkaline substance can be used to increase the pH value of the third mixture and perform the desired alkalization reaction, so as to provide the fourth mixture. The examples of the suitable alkaline substance are all in line with those for step (b), and the alkaline substance used in step (d) can be identical to or different from that used in step (b). In one embodiment of the present invention, sodium hydroxide was used in step (b) and step (d) to perform the alkalization process.

Generally, the fourth mixture provided in step (d) has a pH value of no less than about 11.7, and preferably no less than about 12.5. In one embodiment of the present invention, in the step (d), sodium hydroxide was added into the third mixture to provide a fourth mixture has a pH value of about 11.7.

Then, the neutralizing step (e) is performed, wherein an acid is added into the fourth mixture to decrease the pH value of the fourth mixture, and thus a desired product is provided.

Any suitable acidic substance can be added into the fourth mixture to perform the neutralization reaction and decrease the pH value of the mixture to about 7. Examples of suitable acidic substance are all in line with those for step (c), and the acidic substance used in step (e) can be identical to or different from that used in step (c). In one embodiment of the present invention, hydrochloric acid was used in step (e) to neutralize the fourth mixture.

As showed in the examples provided hereinafter, the product obtained in step (e) of the present invention was enriched in the content of K2 significantly. Therefore, the present invention also provides a method for providing a K2-enriched FU-LING extract.

Optionally, a solid-liquid separation is performed on the third mixture obtained in step (c) to remove the liquid and retain the insoluble, and the retained insoluble is used to perform step (d). The solid-liquid separation can be such as centrifuge and decantation.

The present invention also provides a product obtained from the method of the present invention, wherein the product contains at least one of tumulosic acid, dehydrotumulosic acid, polyporenic acid C and 3-epi-dehydrotumulosic acid, and preferably the product is substantially free of pachymic acid and dehydropachymic acid. The term "substantially free of pachymic acid and dehydropachymic acid" refers to that, the total content of pachymic acid and dehydropachymic acid in a product is no more than about 20 wt %, preferably no more than 10 wt %, more preferably no more than 5 wt %, especially preferably no more than 0.5 wt %, based on the total weight of pachymic acid, dehydropachymic acid, tumulosic acid, dehydrotumulosic acid, polyporenic acid C and 3-epi-dehydrotumulosic acid in the product. In one embodiment of the present invention, the product obtained from the conversion method of the present invention contains pachymic acid and dehydropachymic acid in total of about 0 wt %, i.e., less than 0.5 wt %.

Accordingly, when a FU-LING extract is used as the K1-containing material in the method of the present invention, a FU-LING extract substantially free of pachymic acid and dehydropachymic acid would be provided as the product.

The present invention also provides a use of the product obtained from the conversion method of present invention in the manufacture of a medicament for treating cancers, such as lung cancer, prostate cancer, breast cancer, stomach cancer, and leukemia. In one embodiment of the present invention, the medicament is used for treating lung cancer.

The medicament of the present invention can be in any suitable dosage form depending on the desired administration way. For example, the medicament can be administered by oral or parenteral (e.g., subcutaneous, intravenous, intramuscular, intraperitoneal, or nasal) to a subject in need, but is not limited thereby. Depending on the form and purpose, a suitable carrier can be chosen and used to provide the medicament.

As for the dosage form suitable for oral administration, the medicament provided by the present invention can comprise any pharmaceutically acceptable carrier that will not adversely affect the desired efficiency of the medicament. Examples of the carrier include, for example, solvents (e.g., water, saline, dextrose, glycerol, ethanol or its analogs, or a combination thereof), oily solvents, diluents, stabilizers, absorption retarders, disintegrants, emulsifiers, antioxidants, adhesives, binders, dispersing agents, suspending agents, lubricants, moisture absorbents, and solid carriers (e.g., starch and bentonite). The medicament can be provided in a suitable form for oral administration in any suitable manner, for example, a tablet (e.g., a dragee), a pill, a capsule, a granule, a powder, a fluid extract, a solution, syrup, a suspension, an emulsion, a tincture, etc.

As for the dosage form of injection or drip suitable for subcutaneous, intravenous, intramuscular, or intraperitoneal administration, the medicament provided by the present invention can comprise such as one or more of an isotonic solution, a saline buffer solution (e.g., a phosphate buffer solution or a citrate buffer solution), a solubilizer, an emulsifier, 5% sugar solution, and other carriers to provide the medicament as an intravenous injection, an emulsion intravenous injection, a powder injection, a suspension injection, or a powder-suspension injection. Alternatively, the medicament can be prepared as a pre-injection solid. The pre-injection solid can be provided in a dosage form which is soluble in other solutions or suspensions, or in an emulsifiable dosage form. A desired injection is provided by emulsifying the pre-injection solid or dissolving it in a solution or suspension prior to being administered by the subject in need. In addition, examples of the dosage form for external use which are suitable for nasal or transdermal administration include an emulsion, a cream, gel (e.g., as an aquagel), paste (e.g., a dispersing paste and an ointment), a spray, and a solution (e.g., a washing liquid and a suspension).

Optionally, the medicament provided by the present invention may further comprise a suitable amount of additives, such as a flavoring agent, a toner, or a coloring agent for enhancing the taste and visual perception of the medicament, and a buffering agent, a tackifying agent, a stabilizer, a preservative, a conservative, an antibacterial agent, or an antifungal agent for improving the stability and storability of the medicament. In addition, the medicament may optionally further comprise one or more other active components or be used in combination with a medicament comprising the one or more other active components, to further enhance the effects of the medicament or to increase the application flexibility and adaptability of the preparation thus provided, as long as the other active components have no adverse effect on the desired effect of the medicament. In addition, the inventors of the present invention found that the product obtained from the conversion method of the present invention is effective in inhibiting the growth of cancer cells, especially in inhibiting the growth of lung cancer cells.

Accordingly, the present invention also provides a method for treating cancers. The method comprises administering to a subject in need a therapeutically effective amount of an active ingredient, wherein the active ingredient is the product obtained from the conversion method of the present invention, the FU-LING extract of the present invention, or the medicament prepared by the said product or extract. In one embodiment of the present invention, the method was for treating lung cancer. The dosage form of the product or medicament used in the method for treatment are all in line with the above descriptions.

The present invention will be further illustrated in details with specific examples as follows. However, the following examples are provided only for illustrating the present invention, and the scope of the present invention is not limited thereby.

EXAMPLES

Example 1

A material containing pachymic acid and/or dehydropachymic acid was prepared for used in Example 2. 700 kg of FU-LING medicinal material was extracted for three times by the following procedures. First of all, the FU-LING medicinal material (habitat: Yunnan, China) was soaked in 75% ethanol at a volume ratio of FU-LING medicinal material: 75% ethanol=1:8 to provide a mixture. The mixture was maintained at room temperature for 12 hours. Thereafter, the mixture was heated to boil for 3 hours to provide a liquid extract. The liquid extracts obtained from the above three extractions were combined and filtrated to collect the filtrate. The ethanol contained in the filtrate was removed by vacuum to provide a concentrated solution. The concentrated solution was spray-dried by a spray dryer and an extract was obtained. The components contained in the extract were determined by LC/UV/MS (liquid chromatography coupled to diode array UV detection and mass spectrometry) at 243 nm and 210 nm respectively. The results are shown in FIGS. 1A (243 nm) and 1B (210 nm). Furthermore, the amount and content of each component contained in the extract were determined by high-performance liquid chromatography (HPLC). The results are shown in Table 1.

TABLE 1

| Extract (3250 g) | Amount in extract (g) | Content in extract (%) |
| --- | --- | --- |
| (1) Pachymic acid | 229.78 | 7.07 |
| (2) Dehydropachymic acid | 82.55 | 2.54 |
| (3) Tumulosic acid | 242.78 | 7.47 |

TABLE 1-continued

| Extract (3250 g) | Amount in extract (g) | Content in extract (%) |
|---|---|---|
| (4) Dehydro-tumulosic acid | 122.20 | 3.76 |
| (5) Polyporenic acid C | 52.98 | 1.63 |
| (6) 3-epi-dehydrotumulosic acid | 33.15 | 1.02 |
| (3) + (4) + (5) + (6) | 451.10 | 13.88 |

Figure 1B:
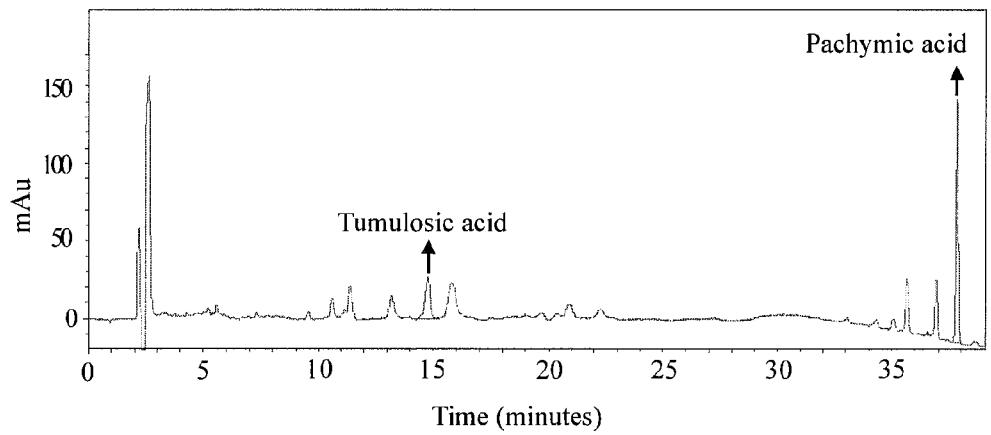
FIG. 1B is an LC/UV/MS spectrum of the raw material used in one embodiment of the conversion method of the present invention at 210 nm, showing the ingredients contained in the raw material.

As shown in FIGS. 1A and 1B and Table 1, the components contained in the extract are triterpenoids such as pachymic acid, dehydropachymic acid, tumulosic acid, dehydrotumulosic acid, polyporenic acid C and 3-epi-dehydrotumulosic acid.

Example 2

Figure 2A:
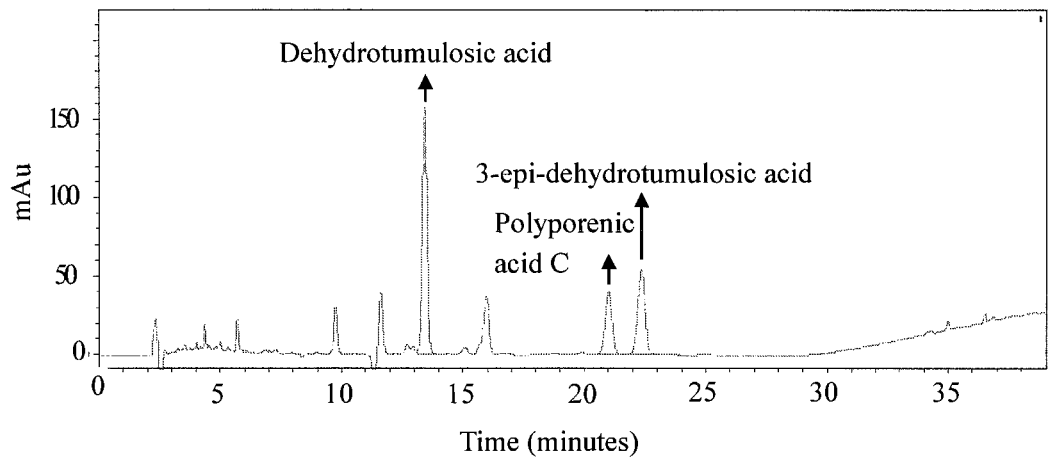
FIG. 2A is an LC/UV/MS spectrum of the product obtained from one embodiment of the conversion method of the present invention at 243 nm, showing the ingredients contained in the product.

3250 g of the extract obtained from Example 1 and pure water were mixed at a volume ratio of extract:water=1:10 with stirring to provide a mixture. Sodium hydroxide was added into the mixture to provide a solution with an alkali concentration of 1N to increase the pH value of the mixture to about 12. Then, the solution was poured into a barrel that was maintained at 70° C. with agitating until the reaction was completed. Thereafter, a concentrated hydrochloric acid (12N) was added into the barrel to neutralize the solution and decrease the pH value of the solution to 7, and then the liquid was removed by centrifugation (1000 rpm) for 30 minutes at room temperature (by a flatbed centrifuge) and the insoluble was collected. The insoluble was washed with pure water and then dried and ground into powder. The powder thus obtained was then extracted three times by 95% ethanol at a volume ratio of insoluble:95% ethanol=1:40, and the extracts obtained from the three extractions were collected and combined, and the combined mixture was concentrated by vacuum to remove ethanol and a product (2000 g) was obtained therefrom. Finally, the components contained in the product were determined by LC/UV/MS at 243 nm and 210 nm respectively. The results are shown in FIGS. 2A (243 nm) and 2B (210 nm). Furthermore, the amount and content of each component contained in the product were determined by HPLC. The results are shown in Table 2.

TABLE 2

| Product (2000 g) | Amount in product (g) | Content in product (%) |
|---|---|---|
| (1) Pachymic acid | 0 | 0 |
| (2) Dehydropachymic acid | 0 | 0 |
| (3) Tumulosic acid | 310.00 | 15.50 |
| (4) Dehydro-tumulosic acid | 131.80 | 6.59 |
| (5) Polyporenic acid C | 48.80 | 2.44 |
| (6) 3-epi-dehydrotumulosic acid | 82.60 | 4.13 |
| (3) + (4) + (5) + (6) | 573.20 | 28.66 |

Example 3

2000 g of the product obtained from Example 2 and pure water were mixed at a volume ratio of extract:water=1:20 with stirring to provide a mixture. Sodium hydroxide was added into the mixture to provide a solution has a pH value of at least more than 11.7. A concentrated hydrochloric acid (12N) was added into the solution to provide a neutral solution with a pH value of 7. Thereafter, the liquid in the neutral solution was removed by centrifugation (1000 rpm) for 30 minutes at room temperature (by a flatbed centrifuge) and the insoluble was collected. The insoluble was washed with pure water and then dried and ground into powder and a K2 composition (500 g) was obtained therefrom. Finally, the amount and content of each component contained in the K2 composition were determined by HPLC. The results are shown in Table 3.

TABLE 3

| K2 composition (500 g) | Amount in K2 composition (g) | Content in K2 composition (%) |
|---|---|---|
| (1) Pachymic acid | 0 | 0 |
| (2) Dehydro-pachymic acid | 0 | 0 |
| (3) Tumulosic acid | 238.60 | 47.72 |
| (4) Dehydrotumulosic acid | 92.10 | 18.42 |
| (5) Polyporenic acid C | 14.65 | 2.93 |
| (6) 3-epi-dehydrotumulosic acid | 4.05 | 0.81 |
| (3) + (4) + (5) + (6) | 349.40 | 69.88 |

Example 4

Another FU-LING medical material (habitat: Yunnan, China) was used to repeat the extraction procedures of Example 1 and provide an extract. The amount and content of each component contained in the extract were determined by HPLC. The results are shown in Table 4.

TABLE 4

| Extract (10 g) | Amount in extract (mg) | Content in extract (%) |
|---|---|---|
| (1) Pachymic acid + Dehydro-pachymic acid | 961.00 | 9.61 |
| (2) Tumulosic acid + Dehydrotumulosic acid | 1123.00 | 11.23 |
| (3) Polyporenic acid C + 3-epi-dehydrotumulosic acid | 265.00 | 2.65 |
| (2) + (3) | 1388.00 | 13.88 |

Example 5

10 g of the extract obtained from Example 4 and pure water were mixed at a volume ratio of extract:pure water=1:10 with stirring to provide a mixture. Sodium hydroxide was added into the mixture to provide a solution has a pH value of to 12. Then, the solution was poured into a round-bottomed flask that was maintained at 60° C. with agitating for 6 hours. Thereafter, a concentrated hydrochloric acid (12N) was added into the round-bottomed flask to neutralize the solution and decrease the pH value of the solution to 7, and then the liquid was removed by centrifugation (1000 rpm) for 30 minutes at room temperature (by a flatbed centrifuge) and the insoluble was collected. The insoluble was washed with pure water and then dried and ground into powder. The powder thus obtained was then extracted three times by 95% ethanol at a volume ratio of insoluble:95% ethanol=1:40, and the extracts obtained from the three extractions were collected and combined, and the combined mixture was concentrated by vacuum to remove ethanol and a product (6.50 g) was obtained therefrom. Finally, the amount and content of each component contained in the product were determined by HPLC. The results are shown in Table 5.

TABLE 5

| Product (6.50 g) | Amount in product (mg) | Content in product (%) |
|---|---|---|
| (1) Pachymic acid + Dehydro-pachymic acid | 2.28 | 0.04 |
| (2) Tumulosic acid + Dehydrotumulosic acid | 1421.55 | 21.87 |
| (3) Polyporenic acid C + 3-epi-dehydrotumulosic acid | 461.26 | 7.10 |
| (2) + (3) | 1882.81 | 28.97 |

Example 6

6.50 g of the product obtained from Example 5 and pure water were mixed at a volume ratio of extract:water=1:20 with stirring to provide a mixture. Sodium hydroxide was added into the mixture to provide a solution has a pH value of 12.0. A concentrated hydrochloric acid (12N) was added into the solution to provide a neutral solution with a pH value of 7. Thereafter, the liquid in the neutral solution was removed by centrifugation (1000 rpm) for 30 minutes at room temperature (by a flatbed centrifuge) and the insoluble was collected. The insoluble was washed with pure water and then dried and ground into powder and a K2 composition (2171.00 mg) was obtained therefrom. Finally, the amount and content of each component contained in the K2 composition was determined by HPLC. The results are shown in Table 6.

TABLE 6

| K2 composition (2171.00 mg) | Amount in K2 composition (mg) | Content in K2 composition (%) |
|---|---|---|
| (1) Pachymic acid + Dehydro-pachymic acid | 0 | 0 |
| (2) Tumulosic acid + Dehydrotumulosic acid | 1317.36 | 60.68 |
| (3) Polyporenic acid C + 3-epi-dehydrotumulosic acid | 62.31 | 2.87 |
| (2) + (3) | 1379.67 | 63.55 |

Example 7

10 g of the extract obtained from Example 4 and pure water were mixed at a volume ratio of extract:pure water=1:10 with stirring to provide a mixture. Sodium hydroxide was added into the mixture to provide a solution has a pH value of 12. Then, the solution was poured into a round-bottomed flask that was maintained at 65° C. with agitating for 2 hours. Thereafter, a concentrated hydrochloric acid (12N) was added into the round-bottomed flask to neutralize the solution and decrease the pH value of the solution to 7, and then the liquid was removed by centrifugation (1000 rpm) for 30 minutes at room temperature (by a flatbed centrifuge) and the insoluble was collected. The insoluble was washed with pure water and then dried and ground into powder. The powder thus obtained was then extracted three times by 95% ethanol at a volume ratio of insoluble:95% ethanol=1:40, and the extracts obtained from the three extractions were collected and combined, and the combined mixture was concentrated by vacuum to remove ethanol and a product (6.20 g) was obtained therefrom. Finally, the components contained in the product were determined by LC/UV/MS at 243 nm and 210 nm respectively. The amount and content of each component contained in the product are shown in Table 7.

TABLE 7

| Product (6.20 g) | Amount in product (mg) | Content in product (%) |
|---|---|---|
| (1) Pachymic acid + Dehydro-pachymic acid | 1.95 | 0.03 |
| (2) Tumulosic acid + Dehydrotumulosic acid | 1313.14 | 21.18 |
| (3) Polyporenic acid C + 3-epi-dehydrotumulosic acid | 461.82 | 7.45 |
| (2) + (3) | 1774.97 | 28.63 |

Example 8

6.20 g of the product obtained from Example 7 and pure water were mixed at a volume ratio of extract:water=1:20 with stirring to provide a mixture. Sodium hydroxide was added into the mixture to provide a solution has a pH value of 12.0. A concentrated hydrochloric acid (12N) was added into the solution to provide a neutral solution with a pH value of 7. Thereafter, the liquid in the neutral solution was removed by centrifugation (1000 rpm) for 30 minutes at room temperature (by a flatbed centrifuge) and the insoluble was collected. The insoluble was washed with pure water and then dried and ground into powder and a K2 composition (2070.80 mg) was obtained therefrom. Finally, the amount and content of each component contained in the K2 composition were determined by HPLC. The results are shown in Table 8.

TABLE 8

| K2 composition (2070.80 mg) | Amount in K2 composition (mg) | Content in K2 composition (%) |
|---|---|---|
| (1) Pachymic acid + Dehydro-pachymic acid | 0 | 0 |
| (2) Tumulosic acid + Dehydrotumulosic acid | 1223.22 | 59.07 |
| (3) Polyporenic acid C + 3-epi-dehydrotumulosic acid | 61.09 | 2.95 |
| (2) + (3) | 1284.31 | 62.02 |

Example 9

10 g of the extract obtained from Example 4 and pure water were mixed at a volume ratio of extract:pure water=1:10 with stirring to provide a mixture. Sodium hydroxide was added into the mixture to provide a solution has a pH value of 12. Then, the solution was poured into a round-bottomed flask that was maintained at 65° C. with agitating for 2.5 hours. Thereafter, a concentrated hydrochloric acid (12N) was added into the round-bottomed flask to neutralize the solution and decrease the pH value of the solution to 7, and then the liquid was removed by centrifugation (1000 rpm) for 30 minutes at room temperature (by a flatbed centrifuge) and the insoluble was collected. The insoluble was washed with pure water and then dried and ground into powder. The powder thus obtained was then extracted three times by 95% ethanol at a volume ratio of insoluble:95% ethanol=1:40, and the extracts obtained from the three extractions were collected and combined, and the combined mixture was concentrated by vacuum to remove ethanol and a product (6.10 g) was obtained therefrom. Finally, the components contained in the product thus obtained were determined by LC/UV/MS at 243 nm and 210 nm respectively. The amount and content of each component contained in the product are shown in Table 9.

TABLE 9

| Product (6.10 g) | Amount in product (mg) | Content in product (%) |
| --- | --- | --- |
| (1) Pachymic acid + Dehydro-pachymic acid | 1.40 | 0.02 |
| (2) Tumulosic acid + Dehydrotumulosic acid | 1294.91 | 21.23 |
| (3) Polyporenic acid C + 3-epi-dehydrotumulosic acid | 450.74 | 7.39 |
| (2) + (3) | 1745.64 | 28.62 |

Example 10

6.10 g of the product obtained from Example 9 and pure water were mixed at a volume ratio of extract:pure water=1:20 with stirring to provide a mixture. Sodium hydroxide was added into the mixture to provide a solution has a pH value of 12.5. A concentrated hydrochloric acid (12N) was added into the solution to provide a neutral solution with a pH value of 7. Thereafter, the liquid in the neutral solution was removed by centrifugation (1000 rpm) for 30 minutes at room temperature (by a flatbed centrifuge) and the insoluble was collected. The insoluble was washed with pure water and then dried and ground into powder and a K2 composition (1952.00 mg) was obtained therefrom. Finally, the amount and content of each component contained in the K2 composition were determined by HPLC. The results are shown in Table 10.

TABLE 10

| K2 composition (1952.00 mg) | Amount in K2 composition (mg) | Content in K2 composition (%) |
| --- | --- | --- |
| (1) Pachymic acid + Dehydro-pachymic acid | 0 | 0 |
| (2) Tumulosic acid + Dehydrotumulosic acid | 1070.67 | 54.85 |
| (3) Polyporenic acid C + 3-epi-dehydrotumulosic acid | 60.71 | 3.11 |
| (2) + (3) | 1131.38 | 57.96 |

Example 11

10 g of the extract obtained from Example 4 and pure water were mixed at a volume ratio of extract:pure water=1:10 with stirring to provide a mixture. Sodium hydroxide was added into the mixture to provide a solution has a pH value of 12. Then, the solution was poured into a round-bottomed flask that was maintained at 65° C. with agitating for 3 hours. Thereafter, a concentrated hydrochloric acid (12N) was added into the round-bottomed flask to neutralize the solution and decrease the pH value of the solution to 7, and then the liquid was removed by centrifugation (1000 rpm) for 30 minutes at room temperature (by a flatbed centrifuge) and the insoluble was collected. The insoluble was washed with pure water and then dried and ground into powder. The powder thus obtained was then extracted three times by 95% ethanol in a volume ratio of insoluble:95% ethanol=1:40, and the extracts obtained from the three extractions were collected and combined, and the combined mixture was concentrated by vacuum to remove ethanol and a product (6.00 g) was obtained therefrom. Finally, the components contained in the product were determined by LC/UV/MS at 243 nm and 210 nm respectively. The amount and content of each component contained in the product are shown in Table 11.

TABLE 11

| Product (6.00 g) | Amount in product (mg) | Content in product (%) |
| --- | --- | --- |
| (1) Pachymic acid + Dehydro-pachymic acid | 0 | 0 |
| (2) Tumulosic acid + Dehydrotumulosic acid | 1272.24 | 21.20 |
| (3) Polyporenic acid C + 3-epi-dehydrotumulosic acid | 443.76 | 7.40 |
| (2) + (3) | 1716.00 | 28.60 |

Example 12

6.00 g of the product obtained from Example 11 and pure water were mixed in a volume ratio of extract:pure water=1:20 with stirring to provide a mixture. Sodium hydroxide was added into the mixture to provide a solution has a pH value of 13.0. A concentrated hydrochloric acid (12N) was added into the solution to provide a neutral solution with a pH value of 7. Thereafter, the liquid in the neutral solution was removed by centrifugation (1000 rpm) for 30 minutes at room temperature (by a flatbed centrifuge) and the insoluble was collected. The insoluble was washed with pure water and then dried and ground into powder and a K2 composition (1884.00 mg) was obtained therefrom. Finally, the amount and content of each component contained in the K2 composition was determined by HPLC. The results are shown in Table 12.

TABLE 12

| K2 composition (1884.00 mg) | Amount in K2 composition (mg) | Content in K2 composition (%) |
| --- | --- | --- |
| (1) Pachymic acid + Dehydro-pachymic acid | 0 | 0 |
| (2) Tumulosic acid + Dehydrotumulosic acid | 1003.98 | 53.29 |
| (3) Polyporenic acid C + 3-epi-dehydrotumulosic acid | 51.06 | 2.71 |
| (2) + (3) | 1055.04 | 56.00 |

Figure 2B:
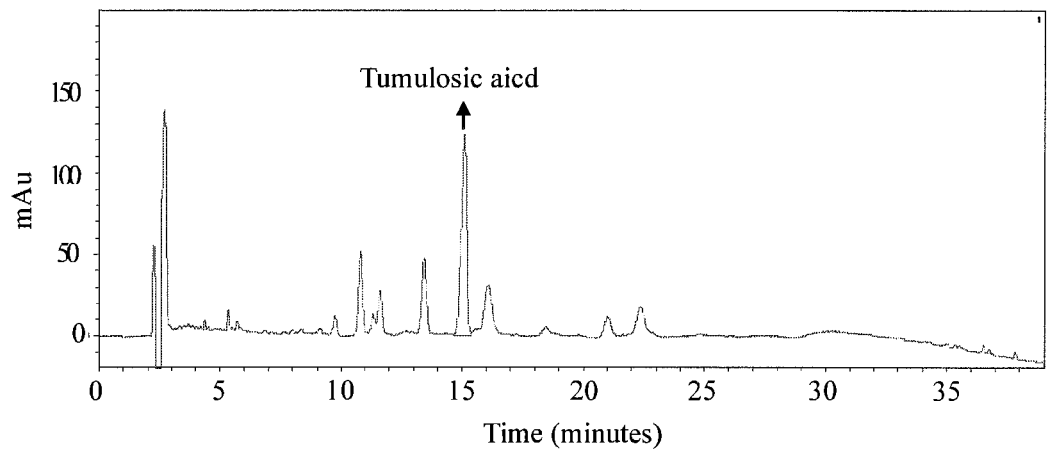
FIG. 2B is an LC/UV/MS spectrum of the product obtained from one embodiment of the conversion method of the present invention at 210 nm, showing the ingredients contained in the product.

As shown in FIGS. 2A and 2B and Tables 1, 2, 4, 5, 7, 9 and 11, the method of the present invention could convert a material containing pachymic acid and dehydropachymic acid into a product containing almost none of pachymic acid and dehydropachymic acid (i.e. the product was free of pachymic acid and dehydropachymic acid). On the other hand, the total amount of tumulosic acid, dehydrotumulosic acid, polyporenic acid C and 3-epi-dehydrotumulosic acid contained in the products obtained from the method of the present invention was increased from 451.10 g to 573.20 g (Tables 1 and 2), from 1388.00 mg to 1882.81 mg (Tables 4 and 5), from 1388.00 mg to 1774.97 mg (Tables 4 and 7), from 1388.00 mg to 1745.64 mg (Tables 4 and 9) and from 1388.00 mg to 1716.00 mg (Tables 4 and 11) respectively; i.e., the total content of tumulosic acid, dehydrotumulosic acid, polyporenic acid C and 3-epi-dehydrotumulosic acid contained in the products was increased from 13.88% to 28.66% (Tables 1 and 2), from 13.88% to 28.97% (Tables 4 and 5), from 13.88% to 28.63% (Tables 4 and 7), from 13.88% to 28.62% (Tables 4 and 9) and from 13.88% to 28.60% (Tables 4 and 11), respectively. These results reveal that the method of the present invention can effectively convert pachymic acid and dehydropachymic acid into tumulosic acid, dehydrotumulosic acid, polyporenic acid C and/or 3-epi-dehydrotumulosic acid. Furthermore, as shown in Tables 1, 3, 4, 6, 8, 10 and 12, the total content of tumulosic acid, dehydrotumulosic acid, polyporenic acid C and 3-epi-dehydrotumulosic acid was increased from 13.88% to 69.88% (Tables 1 and 3), from 13.88% to 63.55% (Tables 4 and 6), from 13.88% to 62.02% (Tables 4 and 8), from 13.88% to 57.96% (Tables 4 and 10), from 13.88% to 56.00% (Tables 4 and 12). These results reveal that the method of the present invention can further increase the content of tumulosic acid, dehydrotumulosic acid, polyporenic acid C and 3-epi-dehydtotumulosic acid to more than 45%.

Example 13

Effects of Product and K2 Composition Obtained from the Method of the Present Invention on Treating Lung Cancer (13-1) Sample Preparation
(13-1-1) Sample 1

The product obtained from Example 2 (hereinafter referred to as "sample 1") was dissolved in dimethyl sulfoxide (DMSO) to provide a stock solution of sample 1 with a concentration of 40 mg sample 1/ml stock solution.

The stock solution of sample 1 was diluted with DMSO to 400× of the test concentration, and then diluted with a serum-free F12K cell culture medium to 2× of the test concentration to provide sample solutions with sample 1 concentrations of 1, 2, 10 and 20 µg/ml, respectively (hereinafter referring to as "sample 1 sample solution").

(13-1-2) Sample 2

The K2 composition obtained from Example 3 (hereinafter referred to as "sample 2") was dissolved in DMSO to provide a stock solution of sample 2 with a concentration of 40 mg sample 21 ml stock solution.

The stock solution of sample 2 was diluted with DMSO to 400× of the test concentration, and then diluted with a serum-free F12K cell culture medium to 2× of the test concentration to provide sample solutions with sample 2 concentrations of 0.195, 0.391, 0.781, 1.563, 3.125, 6.25, 12.5 and 25 µg/ml, respectively (hereinafter referring to as "sample 2 sample solution").

(13-2) Cytotoxicity Test

10% Fetal bovine serum (purchased from HyClone)-containing F12K cell culture medium (purchased from Life Technologies) was added into a 96-well culture plate (100 µl for each well), and A549 cells (i.e. Human lung adenocarcinoma epithelial cell line) was seeded thereinto at an initial cell number of 3-4×10³ cells per well. After that, 100 µl of sample 1 sample solution (at a concentration of 1, 2, 10 or 20 µg/ml) or sample 2 sample solution (at a concentration of 0.195, 0.391, 0.781, 1.563, 3.125, 6.25, 12.5 or 25 µg/ml) was added into six wells of the culture plate, to provide a final concentration of 0.5, 1, 5 or 10 µg/ml for sample 1, or 0.098, 0.195, 0.391, 0.781, 1.563, 3.125, 6.25 or 12.5 µg/ml for sample 2. And, 100 of F12K cell culture medium was added into six wells of the same culture plate to be served as a control group. The plate was placed into an incubator at 37° C., 5% $CO_2$ to be incubated for 48 hours.

Figure 3A:
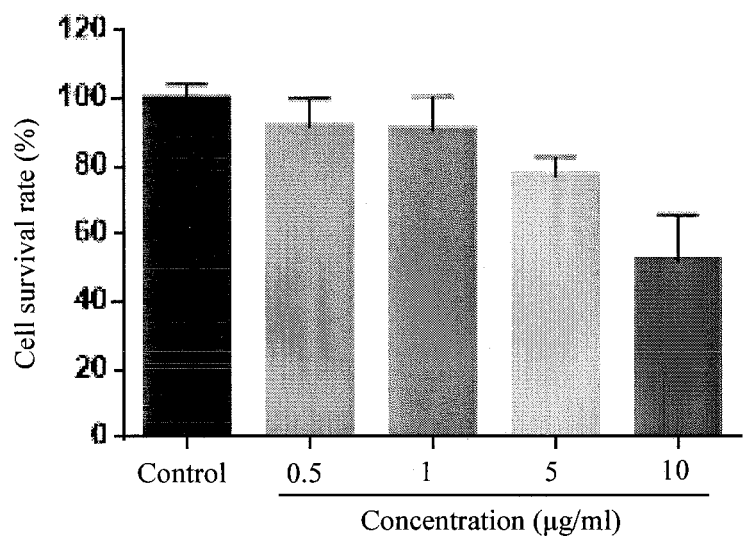
FIG. 3A is a statistical bar diagram showing the survival rate (%) of A549 cells treated with a F12K medium containing different concentrations (i.e., 0.5, 1, 5, and 10 μg/ml) of the product obtained from the conversion method of the present invention for 48 hours respectively, wherein the vertical axis represents the relative cell survival rate (%) of each experimental group as compared to that of control group (i.e., A549 cells treated with F12K medium without the product obtained from the conversion method of the present invention)
Figure 3B:
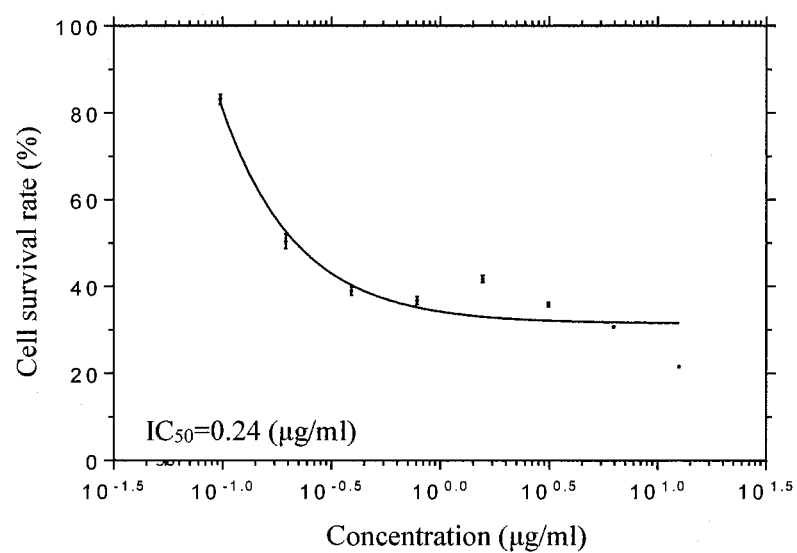
FIG. 3B is a curve diagram showing the survival rate of A549 cells treated with the K2-enriched FU-LING extract of the present invention for 48 hours, wherein the vertical axis represents the survival rate (%) of A549 cells, and the horizontal axis represents the concentrations (μg/ml) of the K2-enriched FU-LING extract of the present invention.

Then, 20 µl of 3-(4,5-dimethylthiazol-2-yl)-2,5-diphenyl tetrazolium bromide (MTT) analytic reagent (5 mg/ml) was added into each well and the cells were incubated at 37° C., 5% $CO_2$ for 4 hours. After that, the culture medium was removed from each well, and 150 µl of DMSO was added into each well and the culture plate was shaken at 600 rpm for 5 minutes. Finally, the absorbance of the sample from each well was measured at a wavelength of 570 nm ($OD_{570nm}$) by a microplate reader. And then, the absorbances obtained from the six repeats of each experimental group (i.e., of the same concentration of sample 1 or sample 2) were calculated to obtain an average absorbance. The average absorbance of the control group was served as a reference to calculate the relative survival rate of cell in each experimental group. The aforementioned experiment process was repeated, and an average value of relative survival rate was obtained from the two repeated processes. The results are shown in FIGS. 3A and 3B. As shown in FIG. 3A, as compared to the control group, the survival rates of A549 cells (i.e. Human lung adenocarcinoma epithelial cell line) treated with 5 and 10 µg/ml sample 1 were decreased to 77.05% and 52.25% respectively. The aforementioned results indicate that sample 1 is effective in treating lung cancer. As shown in FIG. 3B, the survival rate of A549 cells was decreased along with the increase of the concentration of sample 2 significantly. The aforementioned results indicate that K2 composition is also effective in treating lung cancer.

As shown in the above results, the product and the K2 composition substantially free of pachymic acid and dehydropachymic acid according to the present invention actually have an excellent and unexpected effect on inhibiting the growth of lung cancer cells ($IC_{50}$ of K2 composition of the present invention is about 0.24 µg/ml), and thus can be used for treating lung cancer. On the other hand, the $IC_{50}$ of pachymic acid is about 40 µg/ml and that of polyporenic acid C is about 15 µg/ml, seen "Pachymic acid inhibits cell growth and modulates arachidonic acid metabolism in nonsmall cell lung cancer A549 cells. *Molecular Carcinogenesis*. Volume 49, Issue 3, pages 271-282 (2010)" and "Polyporenic acid C induces caspase-8-mediated apoptosis in human lung cancer A549 cells. *Molecular Carcinogenesis*. Volume 48, Issue 6, pages 498-507 (2010)", which are entirely incorporated hereinto by reference.

What is claimed is:

1. A method for providing a K2-enriched FU-LING extract, comprising:
    (a) mixing a FU-LING with a solvent to provide a first mixture;
    (b) alkalizing the first mixture to provide a second mixture;
    (c) acidifying the second mixture to provide a third mixture, which contains K1 of no more than 0.5 wt %, based on the total weight of K1 and K2;
    (d) alkalizing the third mixture to provide a fourth mixture, wherein the fourth mixture has a pH value of more than 7; and
    (e) neutralizing the fourth mixture,
    wherein the K1 is at least one of pachymic acid and dehydropachymic acid, and the K2 is at least one of tumulosic acid, dehydrotumulosic acid, polyporenic acid C and 3-epi-dehydrotumulosic acid.

2. The method as claimed in claim 1, wherein in step (b), the first mixture has a pH value that is increased to no less than about 8 by the alkalization.

3. The method as claimed in claim 1, wherein in step (c), the second mixture has a pH value that is decreased for at least about 3 by the acidification.

4. The method as claimed in claim 1, further comprising performing a solid-liquid separation on the third mixture after the step (c) to remove liquids.

5. The method as claimed in claim 1, wherein the pH value of the fourth mixture is more than 10.

6. A product obtained from the method as claimed in claim 1.

7. The method as claimed is claim 1, wherein the alkalizing reaction in step (b) is performed at a temperature of at least 60° C.

8. The product as claimed in claim 6, which is substantially free of pachymic acid and dehydropachymic acid.

9. The product as claimed in claim 8, wherein tumulosic acid, dehydrotumulosic acid, polyporenic acid C and 3-epi-dehydrotumulosic acid are at a total concentration of 45% or more, based on the total weight of the product.

10. A method for treating a cancer comprising administering to a subject in need a therapeutically effective amount of the product as claimed in claim 6.

11. The method as claimed in claim 10, wherein the subject is suffering from a lung cancer.

12. A method for providing a FU-LING extract by converting K1 into K2, comprising:
 (a) mixing a K1-containing material obtained from FU-LING with a solvent to provide a first mixture;
 (b) alkalizing the first mixture to provide a second mixture at a temperature of at least 60° C.; and
 (c) acidifying the second mixture to provide a third mixture, which contains K1 of no more than 0.5 wt %, based on the total weight of K1 and K2,
 wherein the K1 is at least one of pachymic acid and dehydropachymic acid, and the K2 is at least one of tumulosic acid, dehydrotumulosic acid, polyporenic acid C and 3-epi-dehydrotumulosic acid.

13. The method as claimed in claim 12, wherein in step (b), the first mixture has a pH value that is increased to no less than about 8 by the alkalization.

14. The method as claimed in claim 12, wherein in step (c), the second mixture has a pH value that is decreased for at least about 3 by the acidification.

15. The method as claimed in claim 12, further comprising performing a solid-liquid separation on the third mixture after the step (c) to remove liquids.

16. A product obtained from the method as claimed in claim 12.

17. The product as claimed in claim 16, which is substantially free of pachymic acid and dehydropachymic acid.

18. The product as claimed in claim 17, wherein tumulosic acid, dehydrotumulosic acid, polyporenic acid C and 3-epi-dehydrotumulosic acid are at a total concentration of 45% or more, based on the total weight of the product.

19. A method for treating a cancer comprising administering to a subject in need a therapeutically effective amount of the product as claimed in claim 16.

20. The method as claimed in claim 19, wherein the subject is suffering from a lung cancer.

* * * * *